United States Patent
Fehn et al.

(10) Patent No.: US 6,252,028 B1
(45) Date of Patent: Jun. 26, 2001

(54) CURABLE ORGANOPOLYSILOXANE COMPOSITIONS

(75) Inventors: Armin Fehn, Emmerting; Frank Achenbach, Simbach/Inn, both of (DE)

(73) Assignee: Wacker-Chemie GmbH, München (DE)

( * ) Notice: Subject to any disclaimer, the term of this patent is extended or adjusted under 35 U.S.C. 154(b) by 0 days.

(21) Appl. No.: 09/414,351

(22) Filed: Oct. 7, 1999

(30) Foreign Application Priority Data

Oct. 13, 1998 (DE) .............................. 198 47 097

(51) Int. Cl.$^7$ ................................... C08G 77/08
(52) U.S. Cl. ........................ 528/15; 502/152; 502/213; 525/479
(58) Field of Search ................... 502/152, 213; 528/15; 585/277; 987/10

(56) References Cited

U.S. PATENT DOCUMENTS

| | | |
|---|---|---|
| 4,329,275 | 5/1982 | Hatanaka et al. . |
| 4,645,815 | 2/1987 | Lewis . |
| 5,072,069 | * 12/1991 | Wenski et al. . |
| 5,108,971 | * 4/1992 | Yamazaki et al. . |
| 5,328,974 | 7/1994 | McAfee et al. . |
| 5,525,564 | 6/1996 | McAfee et al. . |
| 5,548,070 | 8/1996 | Dauth et al. . |

FOREIGN PATENT DOCUMENTS

| | | |
|---|---|---|
| 36 35 236 A1 | 5/1987 | (DE) . |
| 44 29 411 A1 | 2/1996 | (DE) . |
| 0 173 512 A2 | 3/1986 | (EP) . |
| 0 363 006 A2 | 4/1990 | (EP) . |
| 0 490 523 A2 | 6/1992 | (EP) . |
| 0 583 159 A2 | 2/1994 | (EP) . |
| 0 638 604 A1 | 2/1995 | (EP) . |

OTHER PUBLICATIONS

The English Derwent Abstract 1996–117700 (13) corresponding to DE 4429411 is enclosed.

Falvello et al., "Synthesis and Crystal Structure of an Unusual Triplatinum Alkynyl–Bridged Complex" Organometallics (1997), 16(6), 1326 (abstract).*

Cross et al., "Formation and Isomerization of Cis–bis(phenylethynyl)bis(tertiarphosphine)platinum Complexes" Journal of the Chemical Society, Dalton Transactions (1986) 1987–92 (abstract).*

Organometallics (1992), No. 11, pp. 2873–2883.

J. Chem. Soc., Dalton Trans. (1986), pp. 1987–1992.

Chemical Abstract, vol. 117, No. 90472, (1992).

* cited by examiner

*Primary Examiner*—Robert Dawson
*Assistant Examiner*—Marc S. Zimmer
(74) *Attorney, Agent, or Firm*—Brooks & Kushman P.C.

(57) ABSTRACT

Curable organopolysiloxane compositions comprising (D) a platinum catalyst selected from the class consisting of

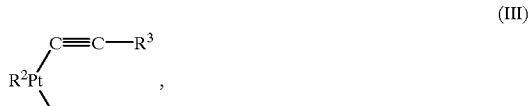

(III)

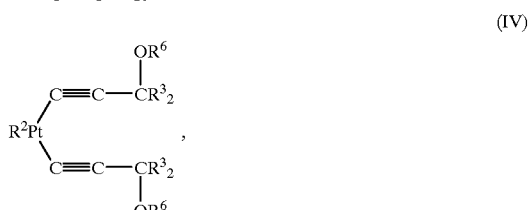

(IV)

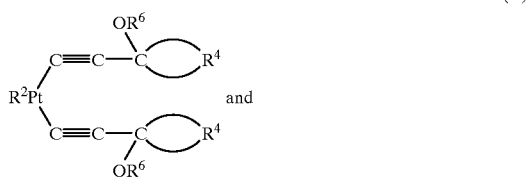

(V)

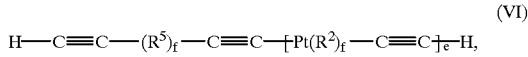

(VI)

where $R^2$ is an unsubstituted or substituted diene bonded to platinum via at least one π bond, having an unbranched or branched chain of from 4 to 12 carbon atoms or a ring of from 6 to 18 carbon atoms, $R^3$ are identical or different and are a hydrogen atom, halogen atom or a monovalent, unsubstituted or halogen- or cyano-substituted hydrocarbon radical having from 1 to 24 carbon atoms, $R^4$ are identical or different bivalent, unsubstituted or substituted hydrocarbon radicals having from 1 to 24 carbon atoms, $R^5$ are identical or different bivalent, unsubstituted or substituted hydrocarbon radicals having from 1 to 12 carbon atoms, silane radicals or siloxane radicals, $R^6$ are identical or different and are a hydrogen atom or a monovalent hydrocarbon radical having from 1 to 20 carbon atoms, e is an integer greater than or equal to 1, and
f is 0 or 1.

15 Claims, No Drawings

CURABLE ORGANOPOLYSILOXANE COMPOSITIONS

TECHNICAL FIELD

The present invention relates to silicone compositions crosslinkable thermally by hydrosilylation, to processes for their preparation, to platinum catalysts used for this purpose, and also to the use of the crosslinkable compositions. More particularly, the present invention pertains to one component addition crosslinkable silicone compositions with improved storage life and crosslinking rates.

BACKGROUND ART

Addition-crosslinking silicone compositions crosslink by reacting aliphatically unsaturated groups with Si-bonded hydrogen (hydrosilylation) in the presence of a catalyst, typically a platinum compound. Because the crosslinking reaction begins at the point when all the essential constituents are simultaneously present, addition-crosslinking silicone compositions have hitherto been prepared almost exclusively in the form of two-part (two component) formulations, where the makeup of the individual components is designed such that all of the three essential constituents are not simultaneously present until the components have been mixed. Usually, one of the components comprises the alkenyl-functional polyorganosiloxane and the platinum catalyst, and the other component comprises the SiH-functional crosslinking agent, if desired in combination with alkenyl-functional polyorganosiloxane. After the individual components have been mixed, complete cure may be effected at room temperature to give a silicone elastomer, although curing usually takes place at an elevated temperature.

The two-part system for addition-crosslinkable silicone compositions is associated with numerous disadvantages, such as logistics, the high risk of contamination by traces of platinum and the necessity for an additional mixing step. Although a ready-to-use composition is obtained once the components have been mixed, this composition has a severely restricted pot life, even at room temperature. This short pot life requires, first, that the composition be used very quickly, and second, frequent cleaning of the storage containers, metering systems, processing machinery, etc. is performed, since any material remaining, for example as a result of back-mixing or adhesion to walls, will ultimately gel.

These disadvantages have encouraged many attempts to provide addition-crosslinking silicone compositions in the form of one-part formulations (IP systems). Since in a 1P system all of the constituents needed for the crosslinking are present together, the problem is fundamentally that of finding some way of suppressing the premature onset of the crosslinking reaction, which normally proceeds significantly even at room temperature. Known methods for controlled adjustment (extension) of the pot life of addition-crosslinking compositions are, for example, the use of inhibitors, which are able to considerably reduce the activity of the platinum catalyst at room temperature. Examples include phosphorus compounds in combination with peroxides as disclosed in U.S. Pat. No. 4,329,275 or azodicarbonyl compounds as disclosed in EP-A-490 523. Varying the type and content of these inhibitors can extend the pot life as desired, but increasing pot life by inhibitor use is also inseparably associated with a disadvantageous effect on crosslinking performance. This applies in particular if the pot life is extended to several months using high inhibitor contents: increased initiation temperatures, low crosslinking rates, and even under-crosslinking are the result.

Another fundamentally different method for extending storage life of 1P systems is to encapsulate the platinum catalyst in a finely divided material which does not release the platinum until the temperature has risen. This can be done, for example, by microencapsulating the platinum catalyst using a thermoplastic silicone resin or an organic thermoplastic, as described, for example, in EP-A-363 006, but this is a relatively complicated procedure. A third method is to select the catalyst from specific platinum complexes whose activity is designed to provide sufficiently rapid hydrosilylation at elevated temperatures, but slow reaction at room temperature such that pot lives of a number of months are achieved. Addition-crosslinking compositions of this type comprising platinum complexes have been described, for example, in EP-A-583 159 and DE-A-36 35 236. Although the compositions described have markedly improved pot lives with, in some cases, sufficiently high crosslinking rates, there remains a need to improve the pot life and crosslinking rate of addition-crosslinking compositions having one-part formulations by using higher performance platinum catalysts without having to accept the disadvantages described above. This object is achieved by the present invention.

SUMMARY OF THE INVENTION

The present invention provides platinum catalysts which, in one-component addition-crosslinkable silicone compositions, exhibit increased storage life at room temperature, and which yet exhibit high crosslinking rate and high degree of crosslinking at elevated temperatures. For the purposes of the present invention the term organopolysiloxanes includes both polymers and oligomers, and also dimeric siloxanes.

DESCRIPTION OF THE PREFERRED EMBODIMENTS

The present invention provides curable organopolysiloxane compositions comprising (A) compounds which have radicals having aliphatic carbon-carbon multiple bonds, (B) organopolysiloxanes having Si-bonded hydrogen atoms, or, (C) organopolysiloxanes which have SiC-bonded radicals having aliphatic carbon-carbon multiple bonds and Si-bonded hydrogen atoms, and (D) a platinum catalyst selected from the class consisting of

(III)

(IV)

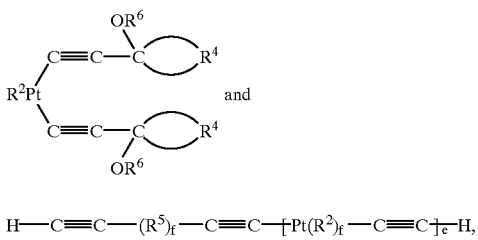

(V)

(VI)

where
R² is an unsubstituted or substituted diene bonded to platinum via at least one π bond, having an unbranched or branched chain having from 4 to 12 carbon atoms or a ring having from 6 to 18 carbon atoms, R³ are identical or different and are a hydrogen atom, halogen atom or a monovalent, unsubstituted or halogen- or cyano-substituted hydrocarbon radical having from 1 to 24 carbon atoms, R⁴ are identical or different bivalent, unsubstituted or substituted, hydrocarbon radicals having from 1 to 24 carbon atoms, R⁵ are identical or different bivalent, unsubstituted or substituted, hydrocarbon radicals having from 1 to 12 carbon atoms, silane radicals or siloxane radicals, R⁶ are identical or different and are a hydrogen atom or a monovalent hydrocarbon radical having from 1 to 20 carbon atoms, e is an integer greater than or equal to 1, and
f is 0 or 1.

If R² is a substituted diene or, respectively, if the radicals R⁴ and R⁵ are substituted hydrocarbon radicals, preferred substituents are halogen atoms, such as F, Cl, Br and I, cyano radicals, —NR⁶₂, and also groups —OR⁶, where R⁶ is as defined above.

The novel formulations may be one-part organopolysiloxane compositions or two-part organopolysiloxane compositions. In the latter case, the two components of the novel compositions may comprise any desired combination of all of the constituents, generally with the proviso that one component does not simultaneously comprise siloxanes having an aliphatic multiple bond, siloxanes having Si-bonded hydrogen and catalyst, i.e. essentially does not simultaneously comprise the constituents (A), (B) and (D) or, respectively, (C) and (D). The novel formulations are preferably one-part compositions.

The compounds (A) and (B) or, respectively, (C) present in the novel compositions are, as is known, selected in such a way as to make crosslinking possible. For example, compound (A) has at least two aliphatically unsaturated radicals and siloxane (B) has at least three Si-bonded hydrogen atoms, or compound (A) has at least three aliphatically unsaturated radicals and siloxane (B) has at least two Si-bonded hydrogen atoms, or else siloxane (C), which has aliphatically unsaturated radicals and Si-bonded hydrogen atoms in the ratios mentioned above, is used instead of compounds (A) and (B). Mixtures of (A), (B), and (C) may also be used. Use of compounds (A) and (B) is preferred, however.

The compound (A) used according to the invention may be a silicon-free organic compounds having preferably at least two aliphatically unsaturated groups, or may be one or more organosilicon compounds having preferably at least two aliphatically unsaturated groups. Examples of organic compounds which can be used in the novel compositions as components (A) are 1,3,5-trivinylcyclohexane, 2,3-dimethyl-1,3-butadiene, 7-methyl-3-methylene-1,6-octadiene, 2-methyl-1,3-butadiene, 1,5-hexadiene, 1,7-octadiene, 4,7-methylene-4,7,8,9-tetrahydroindene, methylcyclopentadiene, 5-vinyl-2-norbornene, bicyclo [2.2.1]hepta-2,5-diene, 1,3-diisopropylbenzene, polybutadiene containing vinyl groups, 1,4-divinylcyclohexane, 1,3,5-triallylbenzene, 1,3,5-trivinylbenzene, 1,2,4-trivinylcyclohexane, 1,3,5-triisopropenylbenzene, 1,4-divinylbenzene, 3-methyl-1,5-heptadiene, 3-phenyl-1,5-hexadiene, 3-vinyl-1,5-hexadiene and 4,5-dimethyl-4,5-diethyl- 1,7-octadiene, N,N'-methylenebis(acrylamide), 1,1,1-tris(hydroxymethyl)propane triacrylate, 1,1,1-tris (hydroxymethyl)propane trimethacrylate, tripropylene glycol diacrylate, diallyl ether, diallylamine, diallyl carbonate, N, N'-diallylurea, triallylamine, tris(2-methylallyl)amine, 2,4,6-trial-lyloxy-1,3,5-triazine, triallyl-s-triazine-2,4,6(1H,3H,5H)trione, diallyl malonate, polyethylene glycol diacrylate, polyethylene glycol dimethacrylate and poly(propylene glycol) methacrylate.

However, the novel silicone compositions preferably comprise, as constituent (A), an aliphatically unsaturated organosilicon compound, and use may be made of any aliphatically unsaturated organosilicon compounds used hitherto in addition-crosslinking compositions, or also, for example, silicone block copolymers having urea segments, silicone block polymers having amide segments and/or having imide segments and/or having ester-amide segments and/or having polystyrene segments and/or having silarylene segments and/or having carborane segments and silicone graft copolymers with ether groups. Mixtures of silicon-containing and non-silicon compounds (A) may also be used.

The organosilicon compound (A) which has SiC-bonded radicals with aliphatic carbon-carbon multiple bonds preferably comprises linear or branched organopolysiloxanes composed of units of the formula $$R_a R^1_b SiO_{(4-a-b)/2} \quad (I)$$

where R are identical or different radicals free from aliphatic carbon-carbon multiple bonds, R¹ are identical or different monovalent, unsubstituted or substituted, SiC-bonded hydrocarbon radicals having an aliphatic carbon-carbon multiple bond, a is 0, 1, 2 or 3, and b is 0, 1 or 2, with the proviso that the sum of a and b is less than or equal to 3 and at least 2 radicals R¹ are present in each molecule.

Radicals R are preferably monovalent hydrocarbon radicals, or may be radicals with a valency of two or more, where the radicals with a valency of two or more, such as bivalent, trivalent and tetravalent radicals, bond a number of siloxy units of the formula (I) to one another, for example, two, three or four siloxy units.

R includes the monovalent radicals —F, —Cl, —Br, —OR⁶, —CN, —SCN, —NCO and SiC-bonded, unsubstituted or substituted hydrocarbon radicals, which may be interrupted by ether oxygen atoms or by the group —C(O)—, or bivalent radicals Si-bonded on both sides as in formula (I).

If the radicals R are SiC-bonded, substituted hydrocarbon radicals, preferred substituents are halogen atoms, phosphorus-containing radicals, cyano radicals, —OR⁶, —NR⁶—, —NR⁶₂, —NR⁶—C(O)—NR⁶₂, —C(O)—NR⁶₂, —C(O)—R⁶, —C(O)OR⁶, —SO₂—Ph and —C₆F₅, in which R⁶ is as defined above and Ph is the phenyl radical.

Examples of radicals R are alkyl radicals such as the methyl, ethyl, n-propyl, isopropyl, n-butyl, isobutyl, tert-butyl, n-pentyl, isopentyl, neopentyl and tert-pentyl radicals; hexyl radicals such as the n-hexyl radical; heptyl radicals such as the n-heptyl radical; octyl radicals such as the n-octyl and isooctyl radicals, for example the 2,2,4-trimethylpentyl radical; nonyl radicals such as the n-nonyl radical; decyl radicals such as n-decyl radical; dodecyl radicals such as the n-dodecyl radical; and octadecyl radicals such as the n-octadecyl radical; cycloalkyl radicals such as cyclopentyl, cyclohexyl, cycloheptyl and methylcyclohexyl radicals; aryl radicals such as the phenyl, naphthyl, anthryl and phenanthryl radicals; alkaryl radicals, such as o-, m- and p-tolyl radicals, xylyl radicals, and ethylphenyl radicals; and aralkyl radicals such as the benzyl radical and the α- and the β-phenylethyl radicals.

Examples of substituted radicals R are haloalkyl radicals such as the 3,3,3-trifluoro-n-propyl radical, the 2,2,2',2',2'-hexafluoroisopropyl radical, the heptafluoroisopropyl radical, haloaryl radicals, such as the o—, m— and p-chlorophenyl radicals, —(CH$_2$)$_n$—N(R$^6$)C(O)NR$^6$$_2$, —(CH$_2$)$_n$—C(O)NR$^6$$_2$, —(CH$_2$)$_n$—C(O)R$^6$, —(CH$_2$)$_6$—C(O)OR$^6$, —(CH$_2$)$_n$—C(O)NR$^6$$_2$, —(CH$_2$)$_n$—C(O)—(CH$_2$)$_m$—C(O)CH$_3$, —(CH$_2$)$_n$—O—CO—R$^6$, —(CH$_2$)$_n$—NR$^6$—(CH$_2$)$_m$—NR$^6$$_2$, —(CH2)$_n$—O—(CH2)$_m$—CH2)$_m$—CH(OH)—CH$_2$OH, —(CH$_2$)$_n$—(OCH$_2$CH$_2$)$_m$—OR$^6$, —(CHD$_2$)$_n$—SO$_2$—Ph and —(CH2)$_n$—O—C$_6$F$_5$, where R$^6$ has one of the meanings given above, n and m are identical or different integers from 0 to 10 and Ph is the phenyl radical.

Examples of R as bivalent radicals Si-bonded on both sides as in formula (I) are those derived from the monovalent examples given above for radical R in that an additional bond substitutes a hydrogen atom. Examples of radicals of this type are —(CH$_2$)$_n$—, —CH(CH$_3$)—, —C(CH$_3$)$_2$—, —CH(CH$_3$)—CH$_2$—, —C$_6$H$_4$—, —CH(Ph)—CH$_2$—, —C(CF$_3$)$_2$—, —(CH$_2$)$_n$—C$_6$H$_4$—(CH2)$_n$—, —(CH$_2$)$_n$—C$_6$H$_4$—C$_6$H$_4$—(CH$_2$)$_n$—, —(CH$_2$O)$_m$—, —(CH$_2$CH$_2$O)$_m$—and —(CH2)$_n$—O$_x$—C$_6$H$_4$—SO$_2$—C$_6$H$_4$—O$_x$—(CH$_2$)$_n$—, where x is 0 or 1, m and n are as defined above, and Ph is the phenyl radical.

The radical R is preferably a monovalent, SiC-bonded, unsubstituted or substituted hydrocarbon radical having from 1 to 18 carbon atoms and free from aliphatic carbon-carbon multiple bonds, particularly preferably a monovalent, SiC-bonded hydrocarbon radical having from 1 to 6 carbon atoms and free from aliphatic carbon-carbon multiple bonds, and in particular the methyl or phenyl radical.

Radicals R$^1$ may be any desired groups amenable to addition reaction (hydrosilylation) with an SiH-functional compound.

If the radicals R$^1$ are SiC-bonded, substituted hydrocarbon radicals, preferred substituents are halogen atoms, cyano radicals and —OR$^6$, where R$^6$ is as defined above.

R$^1$ are preferably alkenyl or alkynyl groups having from 2 to 16 carbon atoms, such as vinyl, allyl, methallyl, 1-propenyl, 5-hexenyl, ethynyl, butadienyl, hexadienyl, cyclopentenyl, cyclopentadienyl, cyclohexenyl, vinylcyclohexylethyl, divinylcyclohexylethyl, norbornenyl, vinylphenyl or styryl radicals, particularly preferably vinyl, allyl and hexenyl radicals.

The molar mass of the constituent (A) may vary within wide boundaries, for example from 10$^2$ to 10$^6$ g/mol. Constituent (A) may, therefore, for example, be a relatively low-molecular-weight alkenyl-functional oligosiloxane, such as 1,2-divinyltetramethyldisiloxane, but may also be a highly polymerized polydimethylsiloxane having Si-bonded vinyl groups positioned along the chain or terminally, e.g. having a molar mass of 10$^5$ g/mol (number average molecular weight determined by NMR). The structure of the molecules forming the constituent (A) may also vary. In particular, the structure of a higher-molecular-weight, i.e. oligomeric or polymeric, siloxane may be linear, cyclic, branched or even resin-like or network-like. Linear and cyclic polysiloxanes are preferably composed of units of the formula R$_3$SiO$_{1/2}$, R$^1$R$_2$SiO$_{1/2}$, R$^1$RSiO$_{2/2}$ and R$_2$SiO$_{2/2}$, where R and R' are as defined above. Branched and network-like polysiloxanes additionally contain trifunctional and/or tetrafunctional units, where preference is given to those of the formulae RSiO$_{3/2}$, R$^1$SiO$_{2/2}$ and SiO$_{4/2}$. It is, of course, also possible to use mixtures of different siloxanes meeting the criteria for the constituent (A).

The component (A) used particularly preferably comprises vinyl-functional, essentially linear, polydiorganosiloxanes with a viscosity of from 0.01 to 500,000 Pa•s, particularly preferably from 0.1 to 100,000 Pa•s, in each case measured at 25° C.

The organosilicon compound (B) used may be any hydrogen-functional organosilicon compound among those hitherto used in addition-crosslinkable compositions.

The organopolysiloxanes (B) used which have Si-bonded hydrogen atoms are preferably linear, cyclic or branched organopolysiloxanes composed of units of the formula

$$R_cH_dSiO_{(4-c-d)/2} \quad (II)$$

where R are identical or different and are as defined above, c is 0, 1, 2 or 3, and d is 0, 1 or 2, with the proviso that the sum of c and d is less than or equal to 3 and at least two Si-bonded hydrogen atoms are present in each molecule.

The organopolysiloxane (B) used according to the invention preferably contains Si-bonded hydrogen in the range from 0.04 to 1.7% by weight, based on the total weight of the organopolysiloxane (B). The molar mass of the constituent (B) may likewise vary within wide boundaries, for example from 10$^2$ to 10$^6$ g/mol. Constituent (B) may, therefore, for example, be a relatively low-molecular-weight SiH-functional oligosiloxane, such as tetramethyldisiloxane, but may also be a highly polymeric polydimethylsiloxane having SiH groups positioned along the chain or terminally, or a silicone resin having SiH groups. The structure of the molecules forming the constituent (B) may also vary. In particular, the structure of a higher-molecular-weight, i.e. oligomeric or polymeric, SiI-containing siloxane may be linear, cyclic, branched or else resin-like or network-like. Linear and cyclic polysiloxanes are preferably composed of units of the formula R$_3$SiO$_{1/2}$, HR$_2$SiO$_{1/2}$, HRSiO$_{2/2}$ and R$_2$SiO$_{2/2}$, where R is as defined above. Branched and network-like polysiloxanes additionally contain trifunctional and/or tetrafunctional units, preferably those of the formulae RSiO$_{3/2}$, HSiO$_{3/2}$ and SiO$_{4/2}$. It is, of course, also possible to use mixtures of different siloxanes meeting the criteria for the constituent (B). In particular, the molecules forming the constituent (B) may, in addition to the obligatory SiH groups, if desired at the same time also contain aliphatically unsaturated groups. Particular preference is given to the use of low-molecular-weight SiH-functional compounds, such as tetrakis(dimethylsiloxy)silane and tetramethylcyclotetrasiloxane, and also high-molecular-weight SiH-containing siloxanes, such as poly(hydromethyl)siloxane and poly(dimethylhydromethyl) siloxane with a viscosity of from 10 to 10,000 mPa•s at 25° C., or analogous SiH-containing compounds in which some of the methyl groups have been replaced by 3,3,3-trifluoropropyl or phenyl groups.

The amount of constituent (B) present in the novel crosslinkable silicone compositions is preferably such that the molar ratio of SiH groups to aliphatically unsaturated groups is from 0.1 to 20, particularly preferably from 1.0 to 5.0.

The components (A) and (B) used according to the invention are commercially available products or can be prepared by common chemical processes.

Instead of components (A) and (B) the novel compositions may comprise organopolysiloxanes (C) which have aliphatic carbon-carbon multiple bonds and Si-bonded hydrogen atoms, but this is not preferred. Organopolysiloxanes (C) may also be used in admixture with (A), (B), or (A) and (B).

If siloxanes (C) are used they are preferably composed of units of the formula

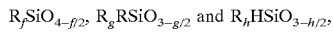

$R_f SiO_{4-f/2}$, $R_g R'SiO_{3-g/2}$ and $R_h HSiO_{3-h/2}$, where R and R' are as defined above, f is 0, 1, 2 or 3, g is 0, 1 or 2, and h is 0, 1 or 2, with the proviso that at least two radicals $R^1$ and at least two Si-bonded hydrogen atoms are present in each molecule.

Examples of organopolysiloxanes (C) are those composed of $SiO_{4/2}$ units, $R_3 SiO_{1/2}$ units, $R_2 R^1 SiO_{1/2}$ units and $R_2 HSiO_{1/2}$ units, so-called MQ resins, and these resins may additionally contain $RSiO_{3/2}$ units and $R_2 SiO$ units, and also linear organopolysiloxanes essentially composed of $R_2 R^1 SiO_{1/2}$ units, $R_2 SiO$ units and RHSiO units, in which R and R' are as defined above.

The organopolysiloxanes (C) preferably have an average viscosity of from 0.01 to 500,000 Pa·s, particularly preferably from 0.1 to 100,000 Pa·s, in each case at 25° C., and can be prepared by common chemical methods.

In the platinum catalysts, examples of $R^2$ are dienes such as 1,3-butadiene, 1,4-diphenyl-1,3-butadiene, 1,3-cyclohexadiene, 1,4-cyclohexadiene, 2,4-hexadiene, 1,4-hexadiene, 1,5-hexadiene, 2,5-dimethyl-2,4-hexadiene, α- or γ-terpines, (R)-(+)-4-isopropenyl-1-methyl-1-cyclohexene, (S)-(−)-4isopropenyl-1-methyl-i-cyclohexene, 4-vinyl-1-cyclohexene, 2,5-heptadiene, 1,5-cyclooctadiene, 1-chloro-1,5-cyclooctadiene, 1,5-dimethyl-1,5-cyclooctadiene, 1,6-dimethyl-1,5-cyclooctadiene, 1,5-dichloro-1,5-cyclooctadiene, 5,8-dihydro-1,4-dioxocin, $\eta^4$-1,3,5,7-cyclooctatetraene, $\eta^4$1,3,5-cycloheptatriene, $\eta^4$-l-fluoro-1,3,5,7-cyclo-octatetraene, $\eta^4$1,2,4,7-tetramethyl-1,3,5,7-cyclooctatetraene, 1,3-dodecadiene, methylcyclopentadiene dimer, 4,7-methylene-4,7,8,9-tetrahydroindene, bicyclo-[4.2.2]deca-3,9-diene-7,8-dicarboxylic anhydride, alkyl bicyclo[4.2.2]deca-3,9-diene-7,8-dicarboxylates and alkyl bicyclo[4.2.2]deca-3,7,9-triene-7,8-di-carboxylates.

The radical $R^2$ is preferably 1,5-cyclooctadiene, 1,5-dimethyl-1,5-cyclooctadiene, 1,6-dimethyl-1,5-cyclooctadiene, 1-chloro-1,5-cyclooctadiene, 1,5-dichloro-1,5-cyclooctadiene, 4-vinyl-1-cyclohexene or $\eta^4$- ,3,5,7-cyclooctatetraene, particularly preferably 1,5-cyclooctadiene, 1,5-dimethyl-1,5-cyclooctadiene and 1,6-dimethyl-1,5-cyclooctadiene.

Examples of $R^3$ are alkyl radicals such as the methyl, ethyl, n-propyl, isopropyl, 1-n-butyl, 2-n-butyl, isobutyl, tert-butyl, n-pentyl, isopentyl, neopentyl and tert-pentyl radicals; hexyl radicals such as the n-hexyl radical; heptyl radicals such as the n- heptyl radical; octyl radicals such as the n-octyl and isooctyl radicals, for example the 2,2,4-trimethylpentyl radical; nonyl radicals such as the n-nonyl radical; decyl radicals such as the n-decyl radical; cycloalkyl radicals such as cyclopropyl, cyclopentyl, cyclohexyl, cycloheptyl and methylcyclohexyl radicals; unsaturated radicals such as the allyl, 5-hexenyl, 7-octenyl, cyclohexenyl or styryl radicals; aryl radicals such as phenyl radicals, o—, m— and p-tolyl radicals, xylyl radicals and ethylphenyl radicals; aralkyl radicals such as the benzyl radical and the α- and β-phenylethyl radicals; and also radicals of the formula $—C(R^7)=CR^7_2$, where $R^7$ are identical or different and are a hydrogen atom, halogen atom or a monovalent, unsubstituted or halo- or cyano-substituted, hydrocarbon radical having from 1 to 21 carbon atoms, such as alkyl radicals having from 1 to 12 carbon atoms, alkenyl radicals, aryl radicals or aralkyl radicals.

Examples of halogenated radicals $R^3$ are haloalkyl radicals, such as the 3,3,3-trifluoro-n-propyl radical, the 2,2,2,2',2',2'-hexafluoroisopropyl radical and the heptafluoroisopropyl radical, and haloaryl radicals, such as the o—, —and p-chlorophenyl radicals.

The radical $R^3$ is preferably a hydrogen atom or hydrocarbon radicals having from 1 to 8 carbon atoms, particularly preferably methyl, ethyl, cyclohexyl or phenyl radicals.

The radical $R^4$ is preferably a bivalent hydrocarbon radicals having from 1 to 12 carbon atoms, e.g. $—CH_2—$, $—C_2H_4—$, $—C_4H_8—$, $—C_5H_{10}—$ or $—C8H_{16}—$, where $—C_5H_{10}—$ is particularly preferred.

The radical $R^5$ is preferably $—CH_2—$, $—C_2H_4—$, $—C_3H_6—$, $—C_4H_8—$, $—C_5H_{10}—$, $—C_6H_4—$, $—C_8H_{16}—$, $—CH_2—N(H)CH_2—$, $—CH_2—O—CH_2—$, $—Si(CH_3)_2—$, $Si(CH_3)_2—[—O—Si(CH_3)_2]_p—$ or $—C_6H_4—Si(CH_3)_2[—O—Si(CH_3)_2]_p—C_6H_4—$, where p are identical or different integers from 1 to 6000. In platinum catalysts of the formula (VI), e is preferably an integer from 1 to 50, particularly preferably an integer from 1 to 10. In catalysts of the formulae (IV) and (V), $R^6$ is preferably a hydrogen atom, alkyl radical or aryl radical, particularly preferably a hydrogen atom or the methyl or the ethyl radical.

A small number of bis(alkynyl)-(η-olefin)platinum compounds and processes for their preparation are known to the skilled worker. In this connection reference may be made, for example, to J. Chem. Soc., Dalton Trans. (1986) 1987–92 and Organometallics (1992) 11 2873–2883.

The platinum catalyst (D) is preferably a bis(alkynyl)(1,5-cyclooctadiene)platinum complex, bis(alkynyl)(1,5-dimethyl-1,5-cyclooctadiene) platinum complex or bis (alkynyl)(1,6-dimethyl-1,5-cycloocta-diene) platinum complex.

The present invention also provides platinum catalysts of the formula (III) in which $R^2$ is 1,5-cyclooctadiene, 1,5-dimethyl-1,5-cyclooctadiene or 1,6-dimethyl-1,5-cyclooctadiene, with the proviso that if $R^2$ is 1,5-cyclooctadiene, $R^3$ is $—C(R^7)=CR^7_2$, wherein $R^7$ is as defined above.

The present invention further provides platinum catalysts of the formulae (IV), (V) and (VI), in which $R^2$ is 1,5-cyclooctadiene, 1,5-dimethyl-1,5-cyclooctadiene or 1,6-dimethyl-1,5-cyclooctadiene.

The amount of the platinum catalyst (D) used according to the invention depends on the desired crosslinking rate and the particular use, and also on economic considerations. The amounts of platinum catalysts (D) present in the novel compositions are such as to give a platinum content of preferably from 0.05 to 500 ppm by weight (=parts by weight per million parts by weight), particularly preferably from 0.5 to 100 ppm by weight, in particular from 1 to 50 ppm by weight, based in each case on the total weight of the composition.

Besides the components (A) to (D) the novel curable formulations may also comprise any other substances included in those used hitherto for preparing addition-crosslinkable compositions.

Examples of reinforcing fillers which may be used as component (E) in the novel compositions are pyrogenic or precipitated silicas with BET surface areas of at least 50 $m^2/g$, and also carbon blacks and activated carbons, such as furnace black and acetylene black, preferably pyrogenic or precipitated silicas with BET surface areas of at least 50 $m^2/g$.

The silica fillers mentioned may have hydrophilic character or have been hydrophobicized by known processes. When incorporating hydrophilic fillers it is necessary to add a hydrophobicizing agent.

The content of actively reinforcing filler (E) in the novel crosslinkable composition is in the range from 0 to 70% by weight, preferably from 0 to 50% by weight.

The novel silicone rubber composition may optionally comprise, as constituent (F), other additives to a proportion of up to 70% by weight, preferably from 0.0001 to 40% by weight. Examples of these fillers are inactive fillers, resin-like polyorganosiloxanes which differ from the siloxanes (A), (B) and (C), dispersants, solvents, coupling agents, pigments, dyes, plasticizers, organic polymers, heat stabilizers, etc. These include additives such as powdered quartz, diatomaceous earth, clays, chalk, lithopones, carbon blacks, graphite, metal oxides, metal carbonates, metal sulfates, metal salts of carboxylic acids, metal dusts, fibers, such as glass fibers or synthetic polymer fibers, synthetic polymer powders, dyes, pigments, etc.

The compositions may furthermore comprise additives (G) which serve for control adjustment of the pot life, initiation temperature and crosslinking rate of the novel compositions. These inhibitors and stabilizers are very well known in the sector of addition-crosslinking compositions. Examples of common inhibitors are acetylenic alcohols, such as I-ethynyl-1-cyclohexanol, 2-methyl-3-butyn-2-ol and 3,5-dimethyl-1-hexyn-3-ol, 3-methyl-1-dodecyn-3-ol, polymethylvinylcyclosiloxanes, such as 1,3,5,7-tetravinyltetramethyltetracyclosiloxane, low-molecular-weight silicones with methylvinylSiO$_{2/2}$ a groups and/or R$_2$vinylSiO$_{1/2}$ end groups, such as divinyltetramethyldisiloxane and tetravinyldimethyldisiloxane, and trialkyl cyanurates, maleate esters, such as diallylmaleate, dimethylmaleate and diethylmaleate, fumarates, such as diallylfumarate and diethylfumarate, organic hydroperoxides, such as cumene hydroperoxide, tert-butyl hydroperoxide and pinane hydroperoxide, organic peroxides, organic sulfoxides, organic amines, diamines and amides, phosphanes and phosphites, nitriles, triazoles, diaziridines and oximes. The effectiveness of these inhibitor additives (G) depends on their chemical structure and therefore has to be determined individually.

The inhibitor content of the novel compositions is preferably from 0 to 50,000 ppm, particularly preferably from 50 to 2000 ppm, in particular from 100 to 800 ppm.

The novel organopolysiloxane compositions may, if required, be emulsified, suspended, dispersed or dissolved in liquids. The novel compositions may, in particular depending on the viscosity of the constituents, and also filler content, be of low viscosity and be pourable, may have a paste-like consistency, may be pulverulent, or else may be conformable high-viscosity compositions, as is well known can be the case for the compositions frequently termed RTV-1, RTV-2, LSR and HTV in technical circles. In particular, the novel compositions may, if they are highly viscous, be prepared in the form of granules. In this case the individual granules may comprise all of the components, or the components D and B used according to the invention may be separately incorporated in different granules. In relation to the elastomeric properties of the novel crosslinked silicone compositions, again the entire spectrum is covered, ranging from extremely soft silicone gels through rubbery materials, to highly crosslinked silicones with glass-like behavior.

The novel organopolysiloxane compositions may be prepared by known processes, such as homogeneous mixing of the individual components. The mixing sequence may be as desired. However, it is preferable for the platinum catalyst (D) to be mixed homogeneously with a mixture made from (A) or (B), and, if desired, (E), (F) and (G). The platinum catalyst (D) used according to the invention may be incorporated here as a solid substance, as a solution in a suitable solvent, or as a so-called masterbatch, i.e., mixed uniformly with a small amount of (A) or (A) with (E).

The components (A) to (G) used according to the invention may in each case be a single type of a component of this type or else a mixture of at least two different types of a component of this type.

The novel compositions crosslinkable by addition of Si-bonded hydrogen to an aliphatic multiple bond may be allowed to crosslink under conditions which are the same as those used for compositions known hitherto crosslinkable by a hydrosilylation reaction. The temperatures are preferably from 100 to 220° C., particularly preferably from 130 to 190° C., and the pressures are preferably from 900 to 1100 hPa. However, higher or lower temperatures and pressures may also be used.

The present invention also provides moldings produced by crosslinking the novel compositions. The novel compositions, and also the crosslinked products produced therefrom according to the invention, may be used for any purpose for which elastomers or, respectively, organopolysiloxane compositions crosslinkable to give elastomers could previously be used. This includes, for example, silicone coating or, respectively, impregnation of any of a variety of substrates, the production of moldings, e.g. by injection molding, vacuum extrusion, extrusion, casting and compression molding, and pour-in-place uses such as sealing, embedding or potting compositions, etc.

The novel crosslinkable compositions have the advantage that they can be prepared in a cost-effective and simple process using easily accessible starting materials. The novel crosslinkable compositions also have the advantage that they may be prepared as one-part formulations which have good storage stability at 25° C. and atmospheric pressure and crosslink rapidly only when the temperature is increased. The novel silicone compositions have the advantage that, if the formulation is prepared as a two-part composition, once the two components have been mixed they give a crosslinkable silicone composition which remains usable for a long period at 25° C. under atmospheric pressure (extremely long pot time) and crosslink rapidly only when the temperature is increased.

In preparing the novel crosslinkable compositions it is highly advantageous that the platinum catalyst (D) of the subject invention is easy to incorporate into the remaining components.

Further advantages of the novel composition is that the crosslinked silicone rubbers prepared therefrom have excellent transparency, and that the hydrosilylation reaction does not become slower as the duration of the reaction increases.

The platinum complexes according to the invention are useful as catalysts for the well known hydrosilylation reaction in organosilicon chemistry, as catalysts for hydrogenation of unsaturated organic compounds or polymers and for oligomerization of acetylene and of other alkynes.

The platinum catalysts according to the invention have the further advantage that, during hydrosilylation, terminal double bonds do not rearrange inward to leave behind low-reactivity isomerized starting material, and the further advantage that no platinum colloids are formed and that their use does not result in any discoloration.

In the examples described below all data on parts and percentages are based on weight unless otherwise stated. Unless otherwise stated the examples below are carried out at atmospheric pressure, i.e. at about 1000 hPa, and at room temperature, i.e. at about 20° C., or at a temperature which results when the reactants are brought together at room temperature without additional heating or cooling.

All of the viscosity data given below are based on a temperature of 25° C.

COD means cycloocta-1,5-diene, Me2COD means a mixture of 1,5-dimethycycloocta-1,5-diene and 1,6-dimethylcycloocta-1,5-diene, Vi means a vinyl radical, Me means a methyl radical, $^t$Bu means a tert-butyl radical and Ph means a phenyl radical.

PREPARATION OF THE CATALYST 1

A suspension of 0.5 g of [PtCl$_2$(COD)] in 30 ml of ethanol was cooled to 0° C. under nitrogen. A freshly prepared solution of 0.27 g of phenylacetylene and sodium ethanolate (prepared from 61.5 mg of sodium and 10 ml of ethanol) was then slowly added dropwise. After about 50 minutes the precipitate was filtered off and recrystallized three times from dichloromethane. This gave 0.614 g of a platinum complex of the following formula:

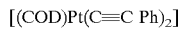

[(COD)Pt(C≡C Ph)$_2$]

PREPARATION OF THE CATALYST 2

A suspension of 0.6 g of [PtCl$_2$(COD)] in 10 ml of ethanol was cooled to 0° C. under nitrogen. A freshly prepared solution of 0.28 g of $^t$Bu-C≡C-H and sodium ethanolate (prepared from 0.07 mg of sodium and 10 ml of ethanol) was then slowly added dropwise, with stirring. After stirring for 2 hours the mixture was evaporated to dryness. The residue was extracted with dichloromethane and evaporated to dryness. After adding n-hexane a colorless powder was obtained. The product was 0.581 g of a platinum complex of the following formula:

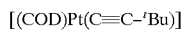

[(COD)Pt(C≡C-$^t$Bu)]

PREPARATION OF THE CATALYST 3

A suspension of 0.48 g of [PtCl$_2$(COD)] in 30 ml of methanol was cooled to –30° C. under nitrogen. A freshly prepared solution of 0.35 g of 1-ethynyl-1-cyclohexanol and 10.6 ml of an approximately 0.5 molar sodium methanolate solution in methanol (commercially available from Aldrich GmbH, Germany) was then slowly added dropwise with stirring. After stirring for 2 hours at from –20 to –15° C. the solution was mixed with 10 ml of water, giving a voluminous precipitate. The precipitate was isolated by filtering through a glass frit, washed with 10 ml of water and 10 ml of diethyl ether and dried for 1.5 hours in vacuo (about 0.1 mbar) at room temperature. This gave 0.642 g of a platinum complex of the following formula:

{(COD)Pt[C≡CC$_6$H$_{10}$(OH)]$_2$}

PREPARATION OF THE CATALYST 4

The procedure described above for preparing catalyst 2 is repeated with the modification that, instead of 0.28 g of $^t$Bu-C≡C-H, 0.28 g of 1-hexyne was used. This gave 0.572 of the platinum complex of the following formula:

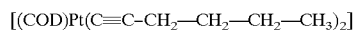

[(COD)Pt(C≡C-CH$_2$—CH$_2$—CH$_2$—CH$_3$)$_2$]

PREPARATION OF THE CATALYST 5

The procedure described above for preparing the catalyst 1 is repeated with the modification that, instead of 0.5 g of [PtCl$_2$(COD)], 0.54 g of [PtCl$_2$(Me$_2$COD)] was used. This gave 0.377 g of the platinum complex of the following formula:

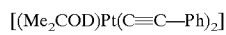

[(Me$_2$COD)Pt(C≡C—Ph)$_2$]

PREPARATION OF THE CATALYST 6

A suspension of 0.48 g of [PtCl$_2$(COD)] in 30 mnl of methanol was cooled to -67° C under nitrogen. A freshly prepared solution of 0.587 g of 1, 1-diphenyl-2-propyn-l-ol and 10.6 ml of an approximately 0.5 molar sodium methanolate solution in methanol was slowly added dropwise with stirring. After stirring for 1 hour the mixture was thawed within a period of 1 hour at -10° C, mixed with 0.34 ml of trimethylsilyl chloride and stirred for 5 minutes. The precipitate was filtered off through a glass frit and washed with 5 ml of methanol, and dried at room temperature in vacuo at 0.1 mbar for 1.5 hours. This gave 0.593 g of the platinum complex of the following formula:

{(COD)Pt[C≡CCPh$_2$(OCH$_3$)]$_2$}

PREPARATION OF THE CATALYST 7

A suspension of 0.48 g of [PtCl$_2$(COD)] in 15 ml of methanol was cooled to -10C under nitrogen. A freshly prepared solution of 0.587 g of 1,1-diphenyl-2-propyn-l-ol and 10.6 ml of an approximately 0.5 molar sodium methanolate solution in methanol was slowly added dropwise, with stirring. After stirring for 5 minutes the solution was thawed at room temperature and stirred for 45 minutes. The precipitate was filtered off through a glass frit and washed with 6 ml of methanol and dried at room temperature in vacuo at 0.1 mbar for 2 hours. This gave 0.788 g of the platinum complex of the following formula:

{(COD)Pt[≡E CCPh$_2$(OCH$_3$)]$_2$}

EXAMPLE 1

50.0 g of a vinyldimethylsiloxy-terminated polydimethylsiloxane with a viscosity of 20 Pa•s, 3 mg of l-ethynyl-1-cyclohexanol in 1.0 g of SiH crosslinker were mixed homogeneously with the aid of a Janke & Kunkel IKA-Labortechnik RE 162 stirrer. The SiH crosslinking agent was a copolymer made from dimethylsiloxy units, methylhydrogensiloxy units and trimethylsiloxy units, having a viscosity of 330 mPa•s and a content of 0.46% by weight of Si-bonded hydrogen. 1.3 mg (corresponding to 10 ppm Pt content, based on the total composition) of catalyst 1 dissolved in 0.5 ml of methylene chloride was then stirred in at room temperature.

EXAMPLE 2

The procedure described in Example 1 is repeated with the modification that, instead of 3 mg of ethynylcyclohexanol, 30 mg of ethynylcyclohexanol were incorporated.

EXAMPLE 3

The procedure described in Example 1 is repeated with the modification that, prior to catalyst addition, 35 mg of 2-phenyl-3-butyn-2-ol (commercially available from Aldrich GmbH & Co KG, Germany) were incorporated instead of the ethynylcyclohexanol.

COMPARATIVE EXAMPLE 1

The procedure described in Example 2 is repeated with the modification that, instead of catalyst 1, 10 ppm of platinum in the form of platinum divinyltetramethyldisiloxane complex in vinyl-terminated polydimethylsiloxane (commercially available from ABCR GmbH & Co, Germany) were used.

EXAMPLE 4

The procedure described in Example 2 is repeated with the modification that, instead of catalyst 1, 1.2 mg (corresponding to 10 ppm platinum content, based on the entire silicone composition) of catalyst 2 were incorporated.

EXAMPLE 5

The procedure described in Example 2 is repeated with the modification that, instead of catalyst 1, 1.4 mg (corresponding to 10 ppm platinum content, based on the entire silicone composition) of catalyst 3 were incorporated.

EXAMPLE 6

The procedure described in Example 2 is repeated with the modification that, instead of catalyst 1, 1.2 mg (corresponding to 10 ppm platinum content, based on the entire silicone composition) of catalyst 4 were incorporated.

EXAMPLE 7

The procedure described in Example 2 is repeated with the modification that, instead of catalyst 1, 1.4 mg (corresponding to 10 ppm platinum content, based on the entire silicone composition) of catalyst 5 were incorporated.

EXAMPLE 8

255 parts by weight of a vinyldimethylsiloxy-terminated polydimethylsiloxane with a viscosity of 20 Pas were charged to a laboratory kneader, heated to 150° C. and mixed with 180 parts by weight of a hydrophobic pyrogenic silica with a specific BET surface area of 300 m$^2$/g and a carbon content of 3.95% by weight. This gave a high-viscosity composition which was then diluted with 165 parts by weight of the abovementioned polydimethylsiloxane. Volatile constituents were removed by kneading in vacuo (10 mbar) at 150° C. for an hour.

488.1 g of the base composition prepared in this way were mixed at a temperature of 25° C. with 0.160 g of inhibitor, 10.95 g of SiH crosslinking agent and 2.0 g of catalyst masterbatch, on a roll mill. The inhibitor was 1-ethynyl-1-cyclohexanol, the SiH crosslinking agent was a copolymer made from methylsiloxy units, methylhydrogensiloxy units and trimethylsiloxy units with a viscosity of 320 mPa•s and a content of 0.48% by weight of Si-bonded hydrogen, and the catalyst masterbatch was a mixture of the abovementioned vinylpolydimethylsiloxane and catalyst 1, platinum content 2.5 ppm based on the entire composition.

COMPARATIVE EXAMPLE 2

The method of operation described in Example 8 is repeated with the modification that the catalyst used comprised 8 ppm of platinum in the form of platinum divinyltetramethyldisiloxane complex in vinyl-terminated polydimethylsiloxane (commercially available from ABCR GmbH & Co, Germany).

EXMAPLE 9

589.4 parts by weight of a vinyldimethylsiloxy-terminated polydimethylsiloxane with a Brabender plasticity of 630 mkp, corresponding to an average molar mass of about 500,000 g/mol, were mixed for 4 hours in a kneader with 252.6 parts by weight of a hydrophobic pyrogenic silica, fed in portions, with a BET specific surface area of 300 m$^2$/g and a carbon content of 3.95% by weight, to give a homogeneous composition.

500 g of the resultant base composition were mixed on a roll mill at a temperature of 20° C. with 0.1 g of inhibitor, 7.5 g of SiH crosslinking agent and 6.5 mg of catalyst 1, dissolved in 1 ml of dichloromethane, to give a homogeneous composition. The inhibitor used was 1-ethynyl-1-cyclohexanol and the SiH crosslinking agent used was a copolymer made from dimethylsiloxy units, methylhydrogensiloxy units and trimethylsiloxy units with a viscosity of 310 mPa•s at 25° C. and a content of 0.46% by weight of Si-bonded hydrogen.

EXAMPLE 10

The procedure described in Example 8 is repeated with the modification that the catalyst used comprised 5 ppm of platinum in the form of platinum catalyst 3 dissolved in 0.5 ml of dichloromethane.

EXAMPLE 11

The procedure described in Example 9 is repeated with the modification that the catalyst used is 5 ppm of platinum in the form of platinum catalyst 3 dissolved in 0.5 ml of dichloromethane.

EXAMPLE 12

The thermal curing properties of the silicone compositions prepared in Examples 1, 2, 3, 4, 5, 6, 7, 13 and 14, and also in Comparative Example 1 (C1), were measured using a Rheometric RDA II Dynamic Analyzer with a heating curve running from 30 to 200° C. and a heating rate of 5° C./minute. For quantitative determination of storage stability the formulations prepared were stored at room temperature (RT) and 50° C., and the time required (measured in days) for doubling of the initial viscosity value was determined. The results of the test are given in Table 1.

The thermal curing properties of the silicone compositions prepared in Examples 8, 9, 10 and 11, and also in Comparative Example 2 (C2), were measured using a Goettfert Elastograph. For quantitative determination of storage stability the formulations prepared were stored at room temperature (RT) and 50° C. and the time required (measured in days) for doubling of the initial viscosity value was determined. The results of the tests are given in Table 2.

TABLE 1

| Example | 1 | 2 | 3 | C1 | 4 | 5 | 6 | 7 | 13 | 14 |
|---|---|---|---|---|---|---|---|---|---|---|
| Initiation temperature [° C.][1] | 114 | 123 | 117 | 96 | 112 | 103 | 113 | 108 | 119 | 109 |
| Storage at RT (days) | >145 | >145 | >125 | 12 | 48 | 66 | 52 | 68 | >24 | >7 |
| Storage at 50° C. (days) | 26 | 85 | 52 | 1 | 3 | 10 | 7 | 4 | >24 | >7 |

[1]The initiation temperature was determined using a heating rate of 5° C./min.

TABLE 2

| Examples | 8 | C2 | 9 | 10 | 11 |
|---|---|---|---|---|---|
| $I_T$ [° C.] | 125 | 116 | 122 | 120 | 119 |
| $t_{90}$ [s] | 32 | 25 | 27 | 28 | 25 |
| Storage at RT (days) | >136 | 15 | >125 | >59 | >59 |
| Storage at 50° C. (days) | 28 | 3 | 25 | 8 | 14 |

The initiation temperature $I_T$ was determined using a heating rate of 10° C./min. The temperature corresponding to 4% of maximum torque was defined as the initiation temperature. The $t_{90}$ value was determined to DIN 53529 T3. The time from the start of curing to 90% ($t_{90}$ value) of the maximum torque was determined here at 180° C.

For further comparison, crosslinked silicone rubber films were prepared from some silicone compositions immediately after preparation, and also after storage of the compositions at room temperature for one month, and their respective mechanical properties determined. The crosslinked silicone rubbers were prepared by crosslinking the mixture of the respective Examples in a hydraulic press at a temperature of 170° C. for 10 minutes to give the silicone rubber. The mechanical tests were carried out on silicone rubber films of, respectively, about 2 and 6 mm thickness after removal from the mold. The result can be found in Table 3.

TABLE 3

| Immediately after preparation | Hardness [Shore A] | UTS [N/mm²] | EB [%] | TPR [N/mm] | RR [%] |
|---|---|---|---|---|---|
| Example 8 | 52 | 10.1 | 590 | 32.1 | 62 |
| Comparison C2 | 50 | 10.7 | 620 | 28.2 | 58 |
| Example 10 | 49 | 10.3 | 600 | 28.9 | 60 |
| Example 9 | 37 | 13.0 | 1140 | 50.0 | 49 |
| Example 11 | 38 | 12.7 | 1070 | 50.9 | 49 |
| Properties after storage for one month | | | | | |
| Example 8 | 50 | 9.5 | 570 | 30.7 | 64 |
| Comparison C2 | *) | *) | *) | *) | *) |
| Example 10 | 51 | 9.9 | 630 | 29.4 | 63 |
| Example 9 | 35 | 12.3 | 1180 | 48.5 | 49 |
| Example 11 | 39 | 13.1 | 1090 | 46.9 | 45 |

*): cured after 15d
Hardness: Shore A hardness was determined according to DIN 53505
UTS: Ultimate tensile strength was determined according to DIN 53504-S1
EB: Elongation at break was determined according to DIN 53504-S1
TPR: Tear propagation resistance was determined according to ASTM D 624
RR: Rebound resilience was determined according to DIN 53512

As can be seen from Table 3, storage for one month resulted in hardly any changes in mechanical properties.

EXAMPLE 13

The procedure described in Example 2 was repeated with the modification that, instead of the catalyst 1, 1.9 mg of catalyst 6 were incorporated by stirring.

EXAMPLE 14

The procedure described in Example 2 was repeated with the modification that, instead of the catalyst 1, 1.8 mg of catalyst 7 were incorporated by stirring.

What is claimed is:

1. A curable organopolysiloxane composition comprising
   (A) compounds which have radicals having aliphatic carbon-carbon multiple bonds,
   (B) organopolysiloxanes having Si-bonded hydrogen atoms, and/or,
   (C) organopolysiloxanes which have SiC-bonded radicals having aliphatic carbon-carbon multiple bonds and Si-bonded hydrogen atoms, wherein said organopolysiloxane composition must contain at least one component (A) or (C) having aliphatic carbon-carbon multiple bonds and at least one organopolysiloxane (B) or (C) having Si-bonded hydrogen, and
   (D) a platinum catalyst selected from the class consisting of

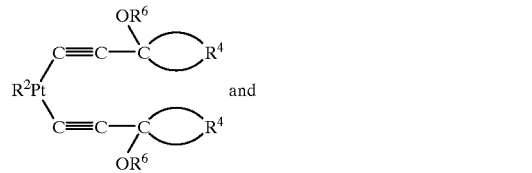

where
$R^2$ is an unsubstituted or substituted diene bonded to platinum via at least one π bond, having an unbranched or branched chain of from 4 to 12 carbon atoms or a ring of from 6 to 18 carbon atoms, $R^3$ are identical or different and are a hydrogen atom, halogen atom or a monovalent, unsubstituted or halogen- or cyano-substituted hydrocarbon radical having from 1 to 24 carbon atoms, $R^4$ are identical or different bivalent, unsubstituted or substituted hydrocarbon radicals having from 1 to 24 carbon atoms, $R^5$ are identical or different bivalent, unsubstituted or substituted hydrocarbon radicals having from 1 to 12 carbon atoms, silane radicals or siloxane radicals, $R^6$ are identical or different and are a hydrogen atom or a monovalent hydrocarbon radical having from 1 to 20 carbon atoms, e is an integer greater than or equal to 1, and f is 0 or 1.

2. A curable polyorganosiloxane composition as claimed in claim 1, wherein constituent (A) is an aliphatically unsaturated organosilicon compound.

3. A curable organopolysiloxane composition as claimed in claim 2, wherein the organosilicon compound (A) used comprises linear or branched organopolysiloxanes composed of units of the formula $$R_a R^1_b SiO_{(4-a-b)/2}$$

where R are identical or different and are monovalent organic radicals free from aliphatic carbon-carbon multiple bonds, $R^1$ are identical or different and are monovalent, unsubstituted or substituted, SiC-bonded hydrocarbon radical having an aliphatic carbon-carbon multiple bond, a is 0, 1, 2 or 3, and b is 0, 1 or 2, with the proviso that the sum of a and b is less than or equal to 3 and at least 2 radicals $R^1$ are present in each molecule.

4. A curable organopolysiloxane composition as claimed in claim 1, wherein radical R is a monovalent SiC-bonded hydrocarbon radical having from 1 to 6 carbon atoms and free from aliphatic carbon-carbon multiple bonds.

5. A curable organopolysiloxane composition as claimed in claim 2, wherein radical R is a monovalent SiC-bonded hydrocarbon radical having from 1 to 6 carbon atoms and free from aliphatiac carbon-carbon multiple bonds.

6. A curable organopolysiloxane composition as claimed in claim 1, wherein the organopolysiloxanes (B) used comprise linear, cyclic or branched organopolysiloxanes composed of units of the formula $$R_c H_d SiO_{(4-c-d)/2} \quad (II)$$

where R are identical or different and are as defmed above, c is 0, 1, 2 or 3, and d is 0, 1 or2, with the proviso that the sum of c and d is less than or equal to 3 and at least two Si-bonded hydrogen atoms are present in each molecule.

7. A curable organopolysiloxane composition as claimed in claim 2, wherein the organopolysiloxanes (B) used comprise linear, cyclic or branched organopolysiloxanes composed of units of the formula $$R_c H_d SiO_{(4-c-d)/2} \quad (II)$$

where R are identical or different and are as defined above, c is 0, 1, 2 or 3, and d is 0, 1 or2, with the proviso that the sum of c and d is less than or equal to 3 and at least two Si-bonded hydrogen atoms are present in each molecule.

8. A curable organopolysiloxane composition as claimed in claim 4, wherein the organopolysiloxanes (B) used comprise linear, cyclic or branched organopolysiloxanes composed of units of the formula $$R_c H_d SiO_{(4-c-d)/2} \quad (II)$$

where R are identical or different and are as defined above, c is 0, 1, 2 or 3, and d is 0, 1 or2, with the proviso that the sum of c and d is less than or equal to 3 and at least two Si-bonded hydrogen atoms are present in each molecule.

9. A curable organopolysiloxane composition as claimed in claim 1, wherein the catalyst (D) comprises a bis(alkynyl) (1,5-cyclooctadiene)platinum complex, bis(alkynyl)(1,5-dimethyl-1,5-cyclooctadiene)platinum complex, bis (alkynyl)(1,6-dimethyl-1,5-cyclooctadiene)platinum complex, or mixture thereof.

10. A curable organopolysiloxane composition as claimed in claim 2, wherein the catalyst (D) comprises a bis(alkynyl) (1,5-cyclooctadiene)platinum complex, bis(alkynyl)(1,5-dimethyl-1,5-cyclooctadiene)platinum complex, bis (alkynyl)(1,6-dimethyl-1,5-cyclooctadiene)platinum complex, or mixture thereof.

11. A curable organopolysiloxane composition as claimed in claim 4 wherein the catalyst (D) comprises a bis(alkynyl) (1,5-cyclooctadiene)platinum complex, bis(alkynyl)(1,5-dimethyl-1,5-cyclooctadiene)platinum complex, bis (alkynyl)(1,6imethyl-1,5-cyclooctadiene)platinum complex, or mixture thereof.

12. A curable organopolysiloxane composition as claimed in claim 6, wherein the catalyst (D) comprises a bis(alkynyl) (1,5-cyclooctadiene)platinum complex, bis(alkynyl)(1,5-dimethyl-1,5-cyclooctadiene)platinum complex, bis (alkynyl)(1,6-dimethyl-1,5-cyclooctadiene)platinum complex, or mixture thereof.

13. A platinum catalyst of the formula (III):

(III)

in which $R^2$ is 1,5-cyclooctadiene, 1,5-dimethyl-1,5-cyclooctadiene or 1,6-dimethyl-1,5-cyclooctadiene, $R^3$ are identical or different and are a hydrogen atom, halogen atom or a monovalent, unsubstituted or halogen- or cyano-substituted hydrocarbon radical having from 1 to 24 carbon atoms, with the proviso that if $R^2$ is 1,5-cyclooctadiene $R^3$ is —C($R^7$)=$CR^7_2$, where $R^7$ are identical or different and are a hydrogen atom, halogen atom or a monovalent, unsubstituted or halogen- or cyano-substituted, hydrocarbon radical having from 1 to 21 carbon atoms.

14. A platinum catalyst of the formulae (IV), (V) or (VI):

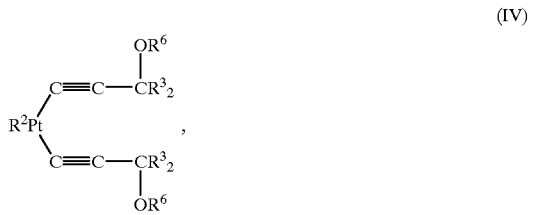

(IV)

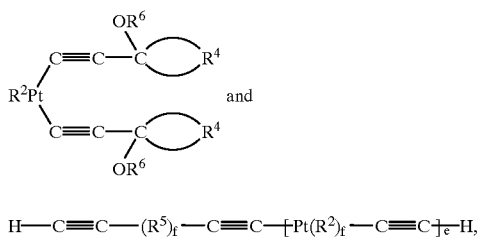

(V)

H—C≡C—(R⁵)_f—C≡C—[Pt(R²)_f—C≡C]_e—H, (VI)

in which $R^2$ is 1,5-cyclooctadiene, 1,5-dimethyl-1,5-cyclooctadiene or 1,6-dimethyl-1,5-cyclooctadiene, $R^3$ are identical or different and are a hydrogen atom, halogen atom or a monovalent, unsubstituted or halogen- or cyano-substituted hydrocarbon radical having from 1 to 24 carbon atoms, $R^4$ are identical or different bivalent, unsubstituted or substituted hydrocarbon radicals having from 1 to 24 carbon atoms, $R^5$ are identical or different bivalent, unsubstituted or substituted hydrocarbon radicals having from 1 to 12 carbon atoms, silane radicals or siloxane radicals, $R^6$ are identical or different and are a hydrogen atom or a monovalent hydrocarbon radical having from 1 to 20 carbon atoms, e is an integer greater than or equal to 1, and f is 0 or 1.

15. A molding produced by crosslinking the composition of claim 1.

* * * * *

UNITED STATES PATENT AND TRADEMARK OFFICE
CERTIFICATE OF CORRECTION

PATENT NO. : 6,252,028 B1  
DATED : June 26, 2001  
INVENTOR(S) : Armin Fehn et al.

Page 1 of 1

It is certified that error appears in the above-identified patent and that said Letters Patent is hereby corrected as shown below:

Column 17, claim 6,
Line 51, delete "defmed" and insert -- defined --.

Signed and Sealed this

Fourth Day of December, 2001

Attest:

NICHOLAS P. GODICI  
Attesting Officer     Acting Director of the United States Patent and Trademark Office